(12) United States Patent
Guenther et al.

(10) Patent No.: US 7,214,285 B2
(45) Date of Patent: May 8, 2007

(54) METHOD OF APPLYING A FASTENER PORTION TO A DIAPER

(75) Inventors: Werner T. Guenther, Neuss (DE); Johann F. Petersen, Grevenbroich (DE); Konstantinos Kourtidis, Drama (GR); Peter Selen, Maasbree (NL)

(73) Assignee: 3M Innovative Properties Company, St. Paul, MN (US)

( * ) Notice: Subject to any disclaimer, the term of this patent is extended or adjusted under 35 U.S.C. 154(b) by 223 days.

(21) Appl. No.: 10/491,775

(22) PCT Filed: Aug. 20, 2002

(86) PCT No.: PCT/US02/26472

§ 371 (c)(1),
(2), (4) Date: Apr. 1, 2004

(87) PCT Pub. No.: WO03/028605

PCT Pub. Date: Apr. 10, 2003

(65) Prior Publication Data

US 2004/0188004 A1   Sep. 30, 2004

(30) Foreign Application Priority Data

Oct. 2, 2001 (EP) .................................. 01123651

(51) Int. Cl.
*A61F 13/15* (2006.01)
*B32B 3/04* (2006.01)
(52) U.S. Cl. ........................ 156/204; 156/216; 156/270
(58) Field of Classification Search ..................... None
See application file for complete search history.

(56) References Cited

U.S. PATENT DOCUMENTS

RE24,906 E    12/1960  Ulrich 4,399,219 A    8/1983   Weaver
4,710,536 A   12/1987  Klingen et al.

(Continued)

FOREIGN PATENT DOCUMENTS

DE          19732499          2/1999

(Continued)

*Primary Examiner*—Richard Crispino
*Assistant Examiner*—Barbara J. Musser
(74) *Attorney, Agent, or Firm*—William J. Bond

(57) ABSTRACT

The present invention relates to a method of applying a fastener portion 10 to an absorbent article 1, said method comprising in a first alternative (A) the steps of: (i) providing a top sheet 2, (ii) placing one or more fastener portions 10 onto an inner surface 2a of the top sheet 2 so that a fastener user's end 12 is essentially supported by the top sheet 2 and a fastener manufacture's end 11 is essentially adjacent to one of the lateral edges 2c,2d of the top sheet 2 whereby the fastening means 15 is facing towards the inner surface 2a of the top sheet 2, (iii) folding around the manufacturer's end 11 so that it is essentially opposite to the user's end 12, and (iv) applying an absorbent core 4 and a back sheet 3 onto the top sheet 2, whereby the sequence of steps (iii) and (iv) may be exchanged, or in a second alternative (B) (i) providing a back sheet 3, (ii) placing one or more fastener portions 10 onto the outer surface 3b of the back sheet 3 so that a fastener user's end 12 is essentially supported by the back sheet 3 and a fastener manufacturer's end 12 is essentially adjacent to one of the lateral edges 3c, 3d of the back sheet 3 whereby the fastening means 15 is facing away from the outer surface 3b of the back sheet 3, (iii) folding over the manufacturer's end 11 so that it is essentially opposite to the user's end 12, and (iv) applying an absorbent core and a top sheet 2 onto the back sheet 3, whereby the sequence of steps (iii) and (iv) may be exchanged.

3 Claims, 8 Drawing Sheets

U.S. PATENT DOCUMENTS

| | | |
|---|---|---|
| 5,344,691 A | 9/1994 | Hanschen et al. |
| 5,354,597 A | 10/1994 | Capik et al. |
| 5,501,679 A | 3/1996 | Krueger et al. |
| 5,527,302 A | 6/1996 | Endres et al. |
| 5,603,797 A | 2/1997 | Thomas et al. |
| 5,681,306 A | 10/1997 | Goulait et al. |
| 5,876,531 A | 3/1999 | Jacobs et al. |
| 5,885,908 A | 3/1999 | Jaeger et al. |
| 6,264,784 B1 | 7/2001 | Menard et al. |
| 6,387,084 B1 | 5/2002 | VanGompel et al. |

FOREIGN PATENT DOCUMENTS

| | | | |
|---|---|---|---|
| DE | 19813334 | | 9/1999 |
| EP | 0 529 681 A1 | | 3/1987 |
| EP | 0 321 232 B1 | | 5/1993 |
| WO | WO 84/04242 | | 11/1984 |
| WO | WO 96/10382 | | 4/1996 |
| WO | WO 98/03140 | | 1/1998 |
| WO | WO 99/03347 | | 1/1999 |
| WO | WO 99/37263 | * | 7/1999 |
| WO | WO 99/51666 | | 10/1999 |

* cited by examiner

US 7,214,285 B2

METHOD OF APPLYING A FASTENER PORTION TO A DIAPER

FIELD OF THE INVENTION

The present invention relates to a method of applying a fastener portion to an absorbent article, and, in particular, to a disposable diaper comprising a back sheet facing outwards, an absorbent core and a top sheet contacting the wearer's skin when the absorbent article is applied to the wearer.

BACKGROUND OF THE INVENTION

Absorbent articles such as disposable diapers are provided with fastener portions which are adhered to the body of the absorbent article through one of its end portions, the so-called manufacturer's end, by means of, for example, an adhesive layer. The opposite end portion of the fastener portion which is usually referred to as user's end, comprises a fastening means such as an adhesive fastening means or a mechanical fastening means to close the absorbent article around the wearer's body and fasten the absorbent article on the body. FIGS. 1a and b show a disposable diaper of the state of the art having an hour-glass shape in an open (FIG. 1a) and in a closed form (FIG. 1b), respectively. It can be seen from FIG. 1b that the diaper comprises an absorbent core 4 between a back sheet 3 and a top sheet 2. The manufacturer's end 11 of the fastener portion 10 is adhered to the side panel 6 of the diaper and the user's end 12 is fastened to the landing zone 5 on the front. waistband portion 7b on the back sheet 3 of the diaper.

EP 0,379,850 discloses a method for manufacturing fastener portions having rounded grip-ends or fingerlifts in order to avoid that the wearer of the diaper is hurt or even cut by sharp-edged fingerlifts. A pair of fastener portions is die-cut continuously from a web of fastener portions, and the fastener portions obtained are applied continuously to the edge portions of two different diapers conveyed side-by-side on a conveyor belt. Other methods for forming a plurality of fastener portions, which can be integrated into continuous manufacturing lines for diapers, are disclosed, for example, in WO 98/03,140, U.S. Pat. No. 5,399,219 and U.S. Pat. No. 5,876,531.

WO 84/04,242 discloses another diaper shape wherein the side panels 6 of the diaper are not integrated into the body portion of the diaper so that such body portion is essentially rectangular. A similar construction is shown, for example, in U.S. Pat. No. 5,527,302. In these constructions, the dimensions of the fastener portions 10 are typically larger than the dimensions of fastener portions used in conjunction with diapers comprising side panels 6 integrated into the body portion of the diaper like those shown in FIGS. 1a and b. The larger dimension of the fastener portions 10 is required in order to provide a reliable and stress-free fit of the diaper comprising no integrated side panels 6, on the wearer. Strip-type fastener portions used in conjunction with integrated side panels 6 like those shown by referral number 10 in FIGS. 1a and b, are often referred to as fastener tapes whereas fastener portions like those disclosed in U.S. Pat. No. 5,527,302 are often referred to as big ear fastener portions.

Fastener portions often comprise in addition to the fastening means an elastic means in order to impart stretchability to the fastener portions. Stretchable fastener portions are disclosed, for example, in U.S. Pat. No. 5,527,302 and in WO 99/03,347.

While fastener portions comprising an elastic means are generally advantageous and tend to improve the fit of the diaper to the wearer, they may exhibit a reduced stiffness in comparison to fastener portions comprising no elastic means. This may adversely affect the handleability of fastener portions comprising an elastic means and render the attachment of such fastener portions to the body portion of a diaper difficult, in particular, under high speed manufacturing operations.

It has also been difficult in prior art to provide a method for applying a fastener portion to a diaper so that the fastener portion is easy to open and is also resistant to undesired, premature opening. EP 0,321,232 discloses, for example, a fastener portion comprising both an adhesive and a mechanical fastening means. The fastener portion is attached to the diaper through its manufacturer's end and then folded over onto the inner surface of the top sheet of the diaper where the adhesive means adheres to the inner surface of the top sheet thereby preventing premature "pop open" ("flagging") of the fastener portion while the absorbent article is still being processed on the diaper line, for example. Flagging of fastener portions may result in disrupturing fastener portions in subsequent processing steps and/or adversely affect the folding of the diaper into a packagable state.

It was therefore an object of the present invention to provide an improved method of applying a fastener portion to absorbent articles which can be effectively applied under high speed manufacturing conditions and/or which does not exhibit the shortcomings of the prior art or exhibit them to a lower degree only.

It was another object of the present invention to provide a fastener portion which when applied to an absorbent article, does not "pop open" prematurely.

Other object of the present invention can be taken from the following detailed description of the invention.

BRIEF DESCRIPTION OF THE INVENTION

The present invention refers to a method of applying a fastener portion 10 to an absorbent article 1 and, in particular, to a disposable diaper, said absorbent article 1 comprising a top sheet web 2 having an inner surface 2a, an outer surface 2b, a first lateral edge 2c and a second lateral edge 2d, a back sheet 3 having an inner surface 3a, an outer surface 3b, a first lateral edge 3c and a second lateral edge 3d, an absorbent core 4 arranged between said top sheet 2 and said back sheet 3, said fastener portion 10 comprising a manufacturer's end 11 for securing said fastener portion 10 to the absorbent article 1 and a user's end 12 comprising a fastener means 15, said method comprising in a first alternative (A) the steps of:

(i) providing a top sheet 2;
(ii) placing one or more fastener portions 10 onto the inner surface 2a of the top sheet 2 so that the user's end 12 is essentially supported by the top sheet 2 and the manufacturer's end 11 is essentially adjacent to one of the lateral edges 2c,2d of the top sheet 2 whereby the fastening means 15 is facing towards the inner surface 2a of the top sheet 2;
(iii) folding around the manufacturer's end 11 so that it is essentially opposite to the user's end 12, and
(iv) applying an absorbent core 4 and a back sheet 3 onto the top sheet 2, whereby the sequence of steps (iii) and (iv) may be exchanged, or in a second alternative (B)

(i) providing a back sheet 3;

(ii) placing one or more fastener portions 10 onto the outer surface 3*b* of the back sheet 3 so that the user's end 12 is essentially supported by the back sheet 3 and the manufacturer's end 11 is essentially adjacent to one of the lateral edges 3*c*, 3*d* of the back sheet 3 whereby the fastening means 15 is facing away from the outer surface 3*b* of the back sheet 3, (iii) folding over the manufacturer's end 11 so that it is essentially opposite to the user's end 12, and (iv) applying an absorbent core and a top sheet 2 onto the back sheet 3, whereby the sequence of steps (iii) and (iv) may be exchanged.

The present invention also refers to a method of applying one or more twin fastener portions 10*a* to an absorbent article 1 and, in particular, to a disposable diaper, said absorbent article 1 comprising a top sheet web 2 having an inner surface 2*a*, an outer surface 2*b*, a first lateral edge 2*c* and a second lateral edge 2*d*, a back sheet 3 having an inner surface 3*a*, an outer surface 3*b*, a first lateral edge 3*c* and a second lateral edge 3*d*, an absorbent core 4 arranged between said top sheet 2 and said back sheet 3, said twin fastener portion 10*a* comprising a first manufacturer's end 11*a*, a first user's end 12*a*, a releasable connection 19, a second user's end 12*b* and a second manufacturer's end 11*b*, wherein the dimensions of the manufacturer's ends 11*a*, 11*b*, the user's ends 12*a*, 12*b* and the releasable connection 19 in cross-direction being selected so that the manufacturer's ends 11*a*, 11*b* can be positioned adjacent to opposite edges 2*c*, 2*d* and/or 3*c*, 3*d* of the top sheet 2 or the back sheet 3, respectively, and wherein the releasable connection 19 can be released to provide two separate fastener portions 10, said method comprising in a first alternative (A) the steps of:

(i) providing a top sheet 2, (ii) placing the one or more twin fastener portions 10*a* onto the inner surface 2*a* of the top sheet 2 so that the user's ends 12*a*, 12*b* and the releasable connection 19 are essentially supported by the top sheet 2 and the manufacturer's ends 11*a*, 11*b* are essentially adjacent to opposite edges 2*c*, 2*d* of the top sheet 2 whereby the fastening means 15*a*, 15*b* are facing towards the inner surface 2*a* of the top sheet 2, (iii) folding around the manufacturer's ends 11*a*, 11*b*, and (iv) applying an absorbent core 4 and a back sheet 3 onto the top sheet 2, whereby the sequence of steps (ii) and (iii) or (iii) and (iv), respectively, may be exchanged, or in a second alternative (B)

(i) providing a back sheet 3, (ii) placing the one or more twin fastener portions 10*a* onto the outer surface 3*b* of the back sheet 3 so that the user's ends 12*a*, 12*b* and the releasable connection 19 are essentially supported by the back sheet 3 and the manufacturer's ends 11*a*, 11*b* are essentially adjacent to opposite edges 3*c*, 3*d* of the back sheet 3 whereby the fastening means 15 are facing outwards, (iii) folding around the manufacturer's ends 11*a*, 11*b*, and (iv) applying an absorbent core 4 and a top sheet 2 onto the back sheet 3, whereby the sequence of steps (ii) and (iii) or (iii) and (iv), respectively, may be exchanged.

The present invention also relates to a twin fastener portion 10*a* comprising in the sequence given in cross-direction a first manufacturer's end 11*a*, a first user's end 12*a*, a releasable connection 19, a second user's end 12*b* and a second manufacturer's end 11*b*, wherein the user's ends 12*a* and 12*b* are directly connected to each other by the releasable connection 19 without any separate part and wherein the releasable connection 19 can be released to provide two separate fastener portions 10.

BRIEF DESCRIPTION OF THE DRAWINGS

FIG. 2 also schematically shows the semi-continuous preparation of pairs of two separate fastener portions 10 comprising applying fastener means 15 from supply rolls 101 and adhesive layers 16 from adhesive coating unit 102 (not shown in FIG. 2) to a continuous web of the backing 20 supplied by rolls 100, and cutting two pairs of fastener portions intermittently with the cut and place applicator 103,104 comprising a vacuum roll 103 and a rotating knive 104.

Figure 5A:
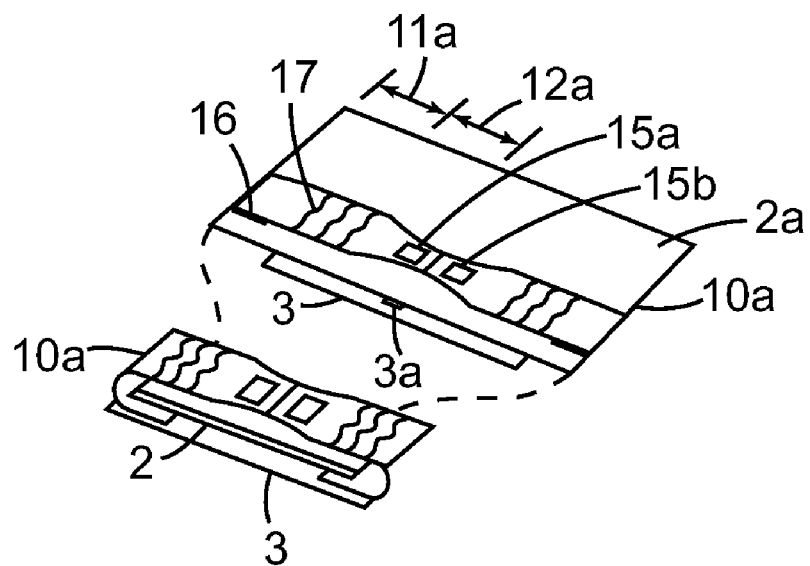
Figure 5B:
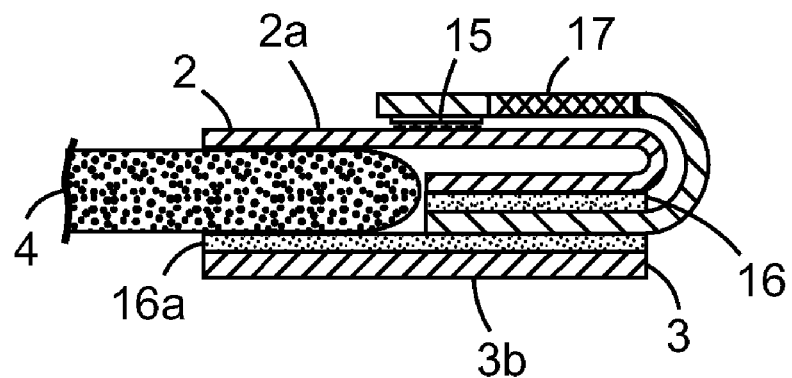
Figure 5C:
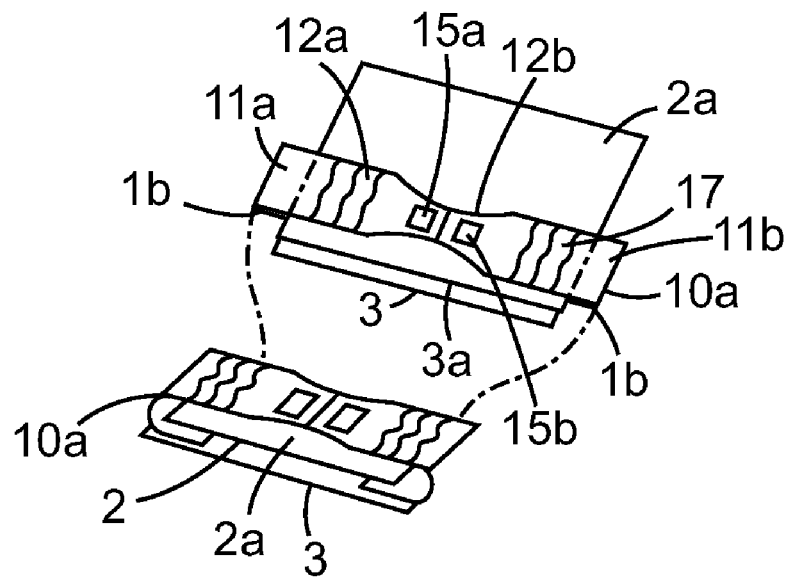
Figure 5D:
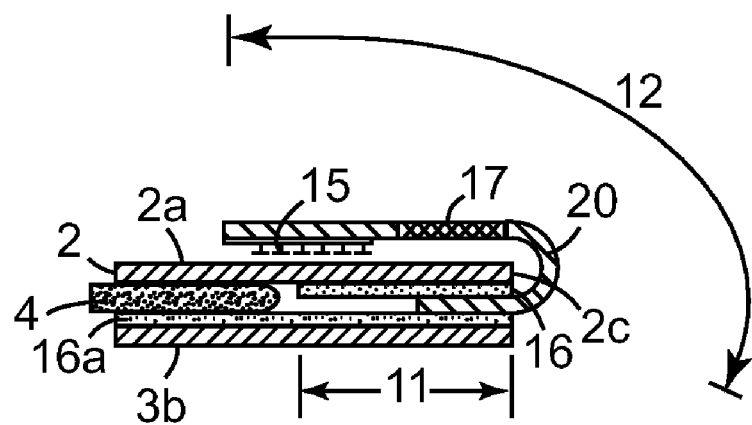

FIG. 5*a* and FIG. 5*c* each are schematic representations of alternatives for arranging the two manufacturer's ends 11*a* of twin fastener portions 10a between the top sheet 2 and the back sheet 3, of the absorbent article whereby FIG. 5b and FIG. 5d, respectively, to give a detailed, cross-sectional view in the cross direction (CD) of the absorbent article through fastener portion 10a to show its anchoring to the absorbent article; the graphical representation of the twin fastener portion 10a only extends to the fastener element 15, the releasable connection 19 is not shown.

Figure 6:
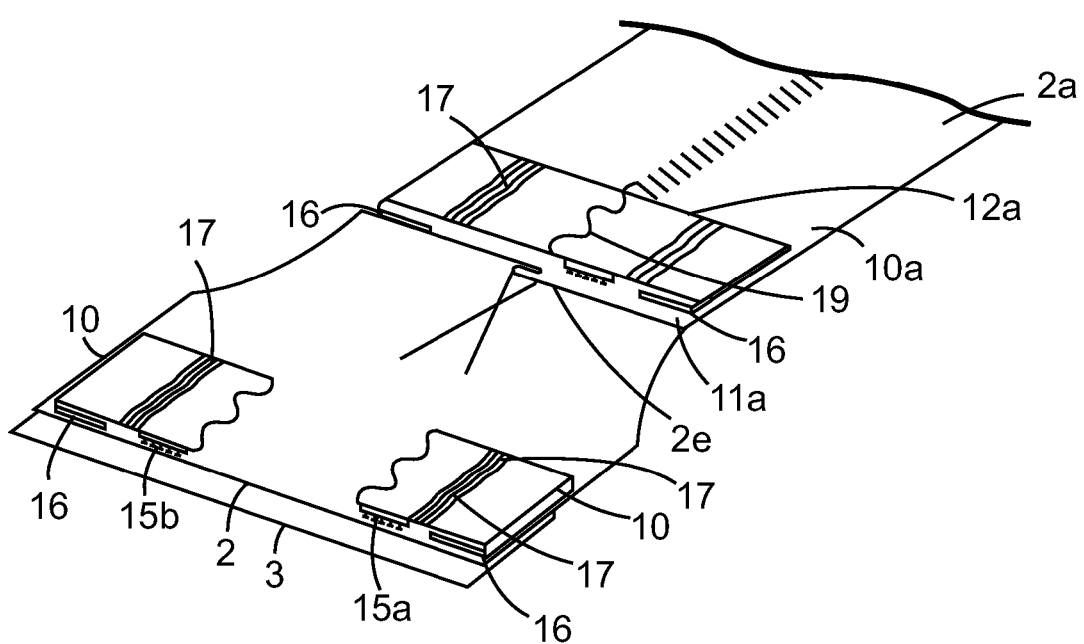

FIG. 6 is a schematic representation of another method according to the present invention comprising providing a top sheet web 2 having an inner surface 2a, an outer surface 2b and a fold 2e, applying a twin fastener portion 10a and folding over its two manufacturer's ends 11a, 11b and adhering them to the inner surface 2a of the top sheet 2, breaking the releasable connection 19 of the twin fastener portion 10a by exerting a force in cross-direction to the top sheet 2 thereby unfolding fold 2e and applying back sheet 3.

DETAILED DESCRIPTION OF THE INVENTION

As used above and below, the term "absorbent article" refers to articles which are placed against or in proximity to the body of the wearer to absorb and contain the various exudates discharged from the body. The absorbent article preferably is disposable, i.e., it is intended to be disposed of after single use and not intended to be laundered or otherwise restored or reused.

A preferred embodiment of the absorbent article referred to in the present invention, is a diaper. The term "diaper" as used above and below refers to a garment generally worn by infants or incontinent persons that is drawn up between the legs and fastened about the waist of the wearer.

As used above and below, the term machine direction (MD) of the absorbent article 1 denotes the direction of the running, continuous web of, for example, the top sheet 2 and the back sheet 3 during the manufacturing of the diaper (see, e.g., FIG. 2) and thus corresponds to the longitudinal direction of the diaper which is normal to the waistband portions 7a, 7b. The cross-direction (CD) is normal to the machine direction. Likewise, the cross-direction (CD) of the fastener portion 10 corresponds to its longitudinal direction, i.e. is the direction pointing from the manufacturer's end 11 to the user's end (compare, e.g., the direction of the running web of the fastener portion in the left part of FIG. 2); the machine direction of the fastener portion is normal to its cross-direction.

The term "adjacent" as used above and below is understood to denote that the manufacturer's end 11 is arranged in proximity of one of the lateral edges of the top sheet 2 or back sheet 3, respectively, whereby a variety of positions is possible. The manufacturer's end may, for example, essentially project over the corresponding lateral edge. It is also possible, however, that the outboard edge of the manufacturer's end in cross-direction essential matches with said lateral edge of the top sheet 2 or back sheet 3, respectively, so that the manufacturer's end 11 is—prior to the step of folding over—essentially supported by the top sheet 2 and/or back sheet 3.

The top sheet 2 comprises an inner surface 2a contacting the wearer's skin and an outer surface 2b facing towards the absorbent core 4. The edges 2c, 2d of the top sheet are formed by the lateral edges of the top sheet in machine direction. Likewise, the back sheet 3 comprises an inner surface 3a facing towards the absorbent core 4, and an outer, exposed surface 3b. The edges 3c, 3d of the back sheet 3 are formed by the lateral edges of the top sheet in machine direction.

Absorbent articles 1 and, in particular, diapers, may have any desired shape such as, for example, a rectangular shape, an I shape, a T shape or an essentially hourglass shape.

Figure 1A:
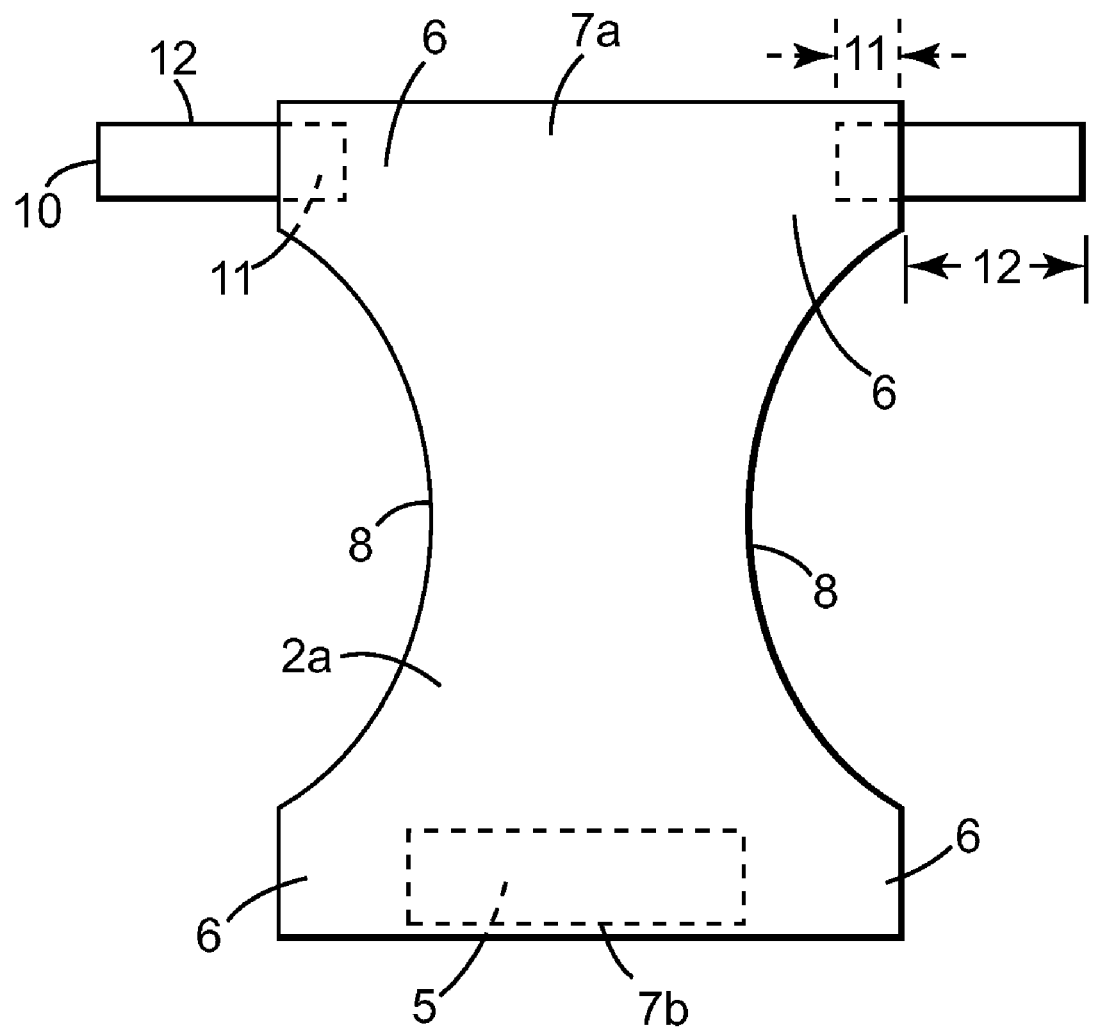
FIG. 1*a* is a schematic representation of a disposable diaper having an hour-glass shape in an open state, said diaper comprising a rear waistband portion 7*a* and a front waistband portion 7*b* which are connected by an intermediate portion comprising the crotch region 8, whereby said waistband portions 7*a*, 7*b* comprise side panels 6. The diaper furthermore comprises fastener portions 10 which are secured through their manufacturer's ends 11 to the side panels 6, while the user's ends 12 are manipulated by the user and secured to the landing zone 5 when applying the diaper to the wearer.
Figure 1B:
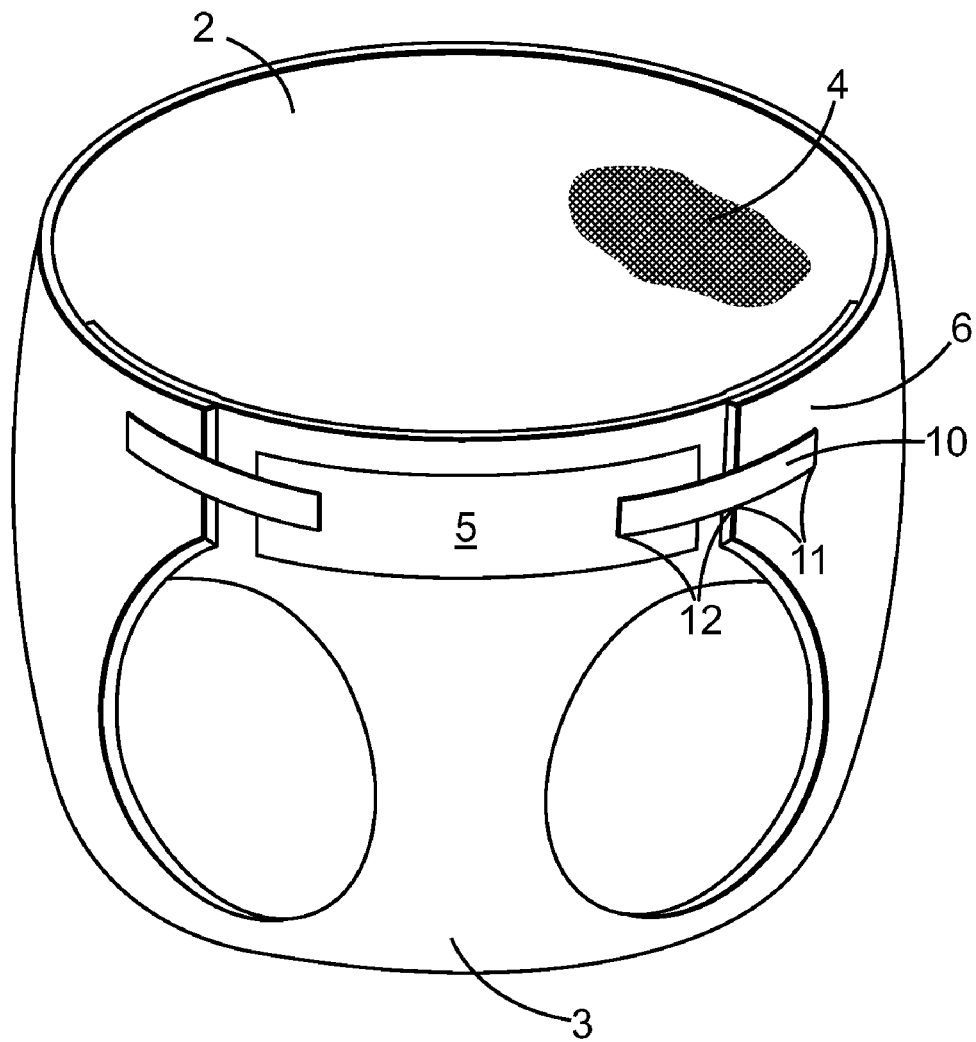
FIG. 1*b* is a schematic representation of the disposable diaper of FIG. 1*a* in a closed form, said diaper comprising an absorbent core 4 between a back sheet 3 and a top sheet 2, and a fastener portions 10 being adhered to the side panels 6 of the diaper through their manufacturer's ends 11 and fastened through their user's end 12 to the landing zone 5 on the front waistband portion 7*b* on the exposed outer surface 3*b* of the back sheet 3.

FIG. 1b is a partially cut-away perspective representation of an essentially hourglass-shaped diaper in a closed form. The diaper comprises an absorbent core 4 between a top sheet 2 and a back sheet 3. The fastener portions 10 are secured through their manufacturer's ends 11 to the outer surface 3b of the rear waistband portion 7a and/or the side panel 6 of back sheet 3. In the closed state of the diaper shown in FIG. 1b, the fastener portions 10 are attached through their user's ends 12 to the target portion 5 on the front waist-band portion 7b of the diaper.

In the various constructions of absorbent articles 1 and diapers, the back sheet 3 generally provides an outer cover member of the absorbent article 1 although sometimes, the absorbent article may comprise a separate outer cover member which is different from the back sheet 3.

The back sheet 3 which has an inner surface 3a and an outer surface 3b facing outwards, i.e., away from the wearer, may comprise a liquid permeable material but preferably comprises a material which is substantially impermeable to liquids. The material of the back sheet 3 is preferably selected so that it prevents exudates contained in the absorbent core 4 from wetting articles such as bed-sheets and overgarments contacting absorbent article 1. For example, thin plastic films such as polypropylene or polyethylene films or other thin films of flexible, liquid-impermeable materials can be preferably used as back sheet 3 of absorbent article 1. Alterative constructions of the back sheet 3 comprise a woven or non-woven fibrous layer which has been totally or partially constructed or treated to impart the desired levels of liquid impermeability to those regions which are adjacent or proximate to the absorbent core 4 in order to prevent the exudates from escaping from the absorbent core. In another embodiment, the back sheet 3 may comprise a microporous, breathable material which permits gases such as water vapour to escape from the absorbent core 4 while effectively preventing liquid exudates from wetting through back sheet 3.

The size and shape of back sheet 3 is typically selected in view of the particular design of the absorbent article, the size and shape of the absorbent core 4 and/or the size and shape of the top sheet 2. The size and shape of the back sheet 3 essentially completely covers the absorbent core 4. If desired, the back sheet 3 may extend, however, beyond the terminal edges of absorbent core 4 and/or top sheet 2 by a selected distance.

The top sheet 2 is preferably selected so that its inner surface 2a is compliant, soft-feeling and non-irritating to the wearer's skin. Top sheet 2 is further selected so that it is liquid pervious permitting liquids to readily penetrate through its thickness. A suitable top sheet 2 may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. Preferably, the top sheet 2 comprises a hydrophobic material to isolate the wearer's skin from liquids retained in the absorbent core 4.

Various woven and non-woven fabrics can be used for top sheet 2. For example, the top sheet may comprise meltblown, spin-bonded or carded polyolefin non-wovens which may preferably have an area weight of between 10–30 g/m$^2$.

The size and shape of the top sheet 2 is typically selected in view of the particular design of the absorbent article 1, the size and shape of the absorbent core 4, the size and shape of the back sheet 3 and the size and shape of the area coming into contact with the wearer's skin. The size and shape of the top sheet 2 may essentially match those of the back sheet 3 but it is also possible that the size and/or shape of the back sheet 3 and the top sheet 2 deviate from each other. In a preferred embodiment, the size and shape of both the back sheet 3 and the top sheet 2 essentially match at least in the area where the fastener portion 10 is applied to the absorbent article whereas the back sheet 3 may extend beyond the top sheet 2 in other areas of the absorbent article 1, or vice versa.

Top sheet 2 and back sheet 3 are connected or otherwise associated together in any operable manner. Top sheet 2 can be affixed directly to back sheet 3 but it is also possible that back sheet 3 and top sheet 2 are connected or joined indirectly with each other by affixing top sheet 2 to intermediate member(s) which in turn are affixed to back sheet 3. Top sheet 2 and back sheet 3 can be connected or affixed directly to each other in the periphery of the absorbent article 1 by, for example, adhesive bonds, sonic bonds, thermal bonds or any other attachment means.

The absorbent core 4 is arranged between the back sheet 3 and the top sheet 2 and has a construction which is generally compressible, conformable, non-irritating to the wearer's skin, and capable of absorbing and retaining liquid body exudates. The absorbent core 4 may comprise, for example, hydrophilic fibrous material and high-absorbing materials and can be provided, for example, in the form of an absorbent pad. The absorbent core 4 may comprise a single, integral piece of material, or alternatively, may comprise a plurality of individual separate pieces of material which are operably assembled together.

The sections on opposed ends of the absorbent article 1 in machine direction which when the absorbent article is applied to the wearer, span around the wearer's waist, are usually referred to as waistband portions 7a, 7b. The absorbent article 1 comprises two waistband portions at its opposed ends in machine direction which form, for example, the front waistband portion 7b and the rear waistband portion 7a, and an intermediate section connecting said two waistband portions. The absorbent article 1 may furthermore comprise side panels 6 which extend in cross-direction from the opposed lateral ends of at least one waistband portion of the back sheet 3 and/or the top sheet 2. The size and the shape of the side panels and their attachment to the back sheet 3 and/or the top sheet 2 can vary broadly. The side panels may form, for example, an integral part of the back sheet 3 and/or the top sheet 2. In alternative configurations, the side panels may be separate members that are connected to back sheet 3 and/or top sheet 2. Side panels may be present at each of the two opposed waistband portions.

The fastener portion 10 allows to releasably and refastenably attach the absorbent article 1 around the wearer's body. The fastener portion 10 comprises a manufacturer's end 11 for securing it to the absorbent article 1 and a user's end 12 comprising a fastener means 15, said user's end being gripped by the user when attaching the absorbent article 1 to the wearer. The manufacturer's end corresponds to the part of the fastener portion which is fixed or secured to the absorbent article during the manufacture of the absorbent article; it usually extends from one of the lateral edges (i.e., the edges in cross-direction) of the fastener portions to a position in cross-direction where the area of anchoring of fastener portions to the diaper as provided during manufacture, ends. The user's end 12 corresponds to the part of the fastener portion 10 which is not anchored to the absorbent article during manufacture; it usually corresponds to the part of the fastener portion which is different from the manufacturer's end 11. This means in other words that the sum of the extensions of the manufacturer's end 11 and the user's end in cross-direction correspond to the extension of the fastener portion 10 in cross-direction. The extension of the user's end 12 in cross-direction preferably is from 55–80% of the extension of the fastener portion 10 in cross-direction whereas the extension of the manufacturer's end 11 correspondingly preferably varies between 45 and 20%.

The size and shape of the fastener portion 10 may vary widely depending on the size, shape and construction of the absorbent article. It is, for example, possible that the fastener portion 10 is formed by a separate fastening tape tab which can be attached to the side panel 6 as is schematically shown in FIG. 1 for the case of a side panel formed integrally by the back sheet 3 and/or top sheet 2. Separate fastening tape strips 10 can be used, however, also in case of non-integral separate side panels. It is also possible, however, that the fastening means 15 is incorporated into the side panel 6 so that the fastener portion 10 is formed by the side panel 6.

The fastener portion 10 may comprise a backing or carrier film 20 which may bear, be bonded to or integrally include, respectively, functional components such as, for example, elastic means 17, fastening means 15, fingerlifts, release tapes to provide a Y-bond between the diaper and the fastener portion, or cover means. The backing and the functional components attached to or incorporated into it, respectively, are selected to impart advantageous properties such as, for example, elasticity, breathability, differential stiffness in machine or cross-direction, respectively, or mechanical or adhesive bonding properties to the fastener portion 10.

The backing may be selected from a variety of films or sheetings including single or multilayered films, coextruded films, laterally laminated films or films comprising foam layers. The layers of such films or sheetings may comprise various materials such, as for example, polypropylene, polyvinylchloride, polyethylene terepthalate, polyethylene, polyolefin copolymers or blends of polyolefins such as, for example, a blend of polypropylene, LPDE (low density polyethylene) and/or LLDPE (linear low density polyethylene), non-woven and foamed materials. The thickness of the backing is preferably between 30 and 500 μm and more preferably between 40 and 150 μm. The base weight of the backing is preferably between 20 and 500 $g/m^2$, more preferably between 40 and 300 $g/m^2$ and especially preferably between 40–200 $g/m^2$.

Figure 3:
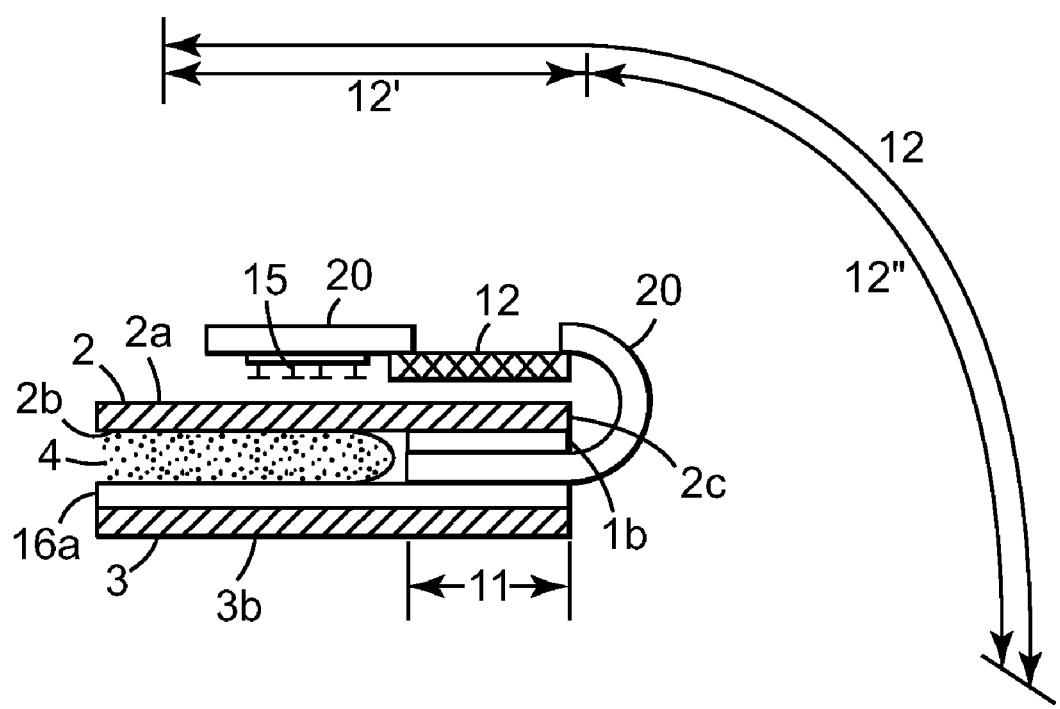
FIG. 3 is a schematic representation of a cross-sectional view of an absorbent article 1 in its cross direction (CD) through fastener portion 10 and gives an enlarged view of the circled portion of the absorbent article marked in FIG. 2. The absorbent article 1 comprises a top sheet 2, a back sheet 3, an absorbent core 4 and the fastener portion 10 whereby the manufacturer's end 11 of said fastener portion 10 is arranged between the outer surface 2*b* of the top sheet 2 and the inner surface 3*a* of the back sheet 3, and whereby the grip portion 12' of the user's end 12 of said fastener portion 10 is arranged on the inner surface 2*a* of said top sheet 2 and comprises mechanical fastening means 15.

The backing 20 preferably comprises at least one elastic means 17 which may, for example, be bonded to the backing 20 as is shown in the specific embodiment of the fastener portion of FIG. 3. Bonding between the elastic means 17 and the backing 20 may be effected by adhesive bonds, sonic bonds, thermal bonds or any other attachment means. The elastic means 17 can also, for example, be included into the backing 20 so that its cross-section essentially matches that of the adjacent part of the backing, i.e., so that there is—different from what is shown in FIG. 3—no step in the bonding area between elastic means 17 and backing 20. Including of one or more elastic means 17 into the fastener portion 10 which renders the fastener portion 10 stretchable in cross-direction (CD) is preferred because it increases the fit and comfort of the absorbent article 1 on the wearer.

The elastic means 17 may be made from a group of materials comprising essentially isotropic or essentially anisotropic materials, respectively. Useful elastic materials preferably exhibit an elongation at break as measured according to ASTM D 882 in the preferred direction of stretchability of at least 50% or more and, more preferably, of more than 100%.

Preferred essentially isotropically elastic materials include elastomeric polyurethane materials, or natural or synthetic rubber materials such as, for example, ethylene-propylene-diene copolymers (EPDM), styrene-butadiene-styrene block copolymers (SBS) or styrene-(ethylene-butylene)-styrene block copolymers (SEBS). Other elastomeric materials which may be used to form the elastic means 17 include elastomeric polyamide materials and elastomeric polyester materials. Preferred elastic materials are commercially available from Exxon Mobil Corp. under the trademark Vector and from Kraton Polymers Comp. under the trademark Kraton.

Attaching an essentially isotropic elastic material to the backing 20 may render the fastener portion 10 unstable or wobbly in the machine direction. Therefore essentially anisotropic elastic materials which allow to provide elasticity to the fastener portion 10 in its cross-direction only, are preferred. Anisotropically elastic materials are described, for example, in U.S. Pat. No. 5,885,908, WO 99/51,666, U.S. Pat. No. 5,344,691, U.S. Pat. No. 5,501,679 and U.S. Pat. No. 5,354,597.

Anisotropically elastomeric materials which are useful in the present invention preferably exhibit a ratio of the F10 force required to stretch a sheet of the elastomeric material (dimensions 20×25 mm) by 10 percent into the machine direction over the F10 forces required in the cross direction, of at least 1.5, more preferably of at least 2.0 and especially preferably of at least 2.5.

The fastener portion 10 comprises a fastening means 15 which may be provided by interlocking, mechanical-type fasteners, by adhesive fastening means and/or by other fastening means. To provide a releasable and refastenable closure system, the absorbent article 1 may comprise in addition to the fastening means 15 a supplemental landing zone 5.

In case the fastening means 15 is of the mechanical type, a landing zone 5 may be required comprising fastening means which are mechanically engagable with fastening means 15 of the fastener portion 10. A suitable mechanical closure system comprises two interlocking means, one of them being a hook (or male) fastener means and the other being a loop (or female) fastener means. The fastening means 15 may comprise the hook fastener or the loop fastener means, respectively, but preferably comprises the hook fastener means. The hook fastener means may have any shape such as hooks, "Ts", "mushrooms" or any other shape as are well known in the art. The hook fastener material may be manufactured from a wide range of materials including nylon, polyester, polyolefins or any combination of these. Preferred hook materials are commercially available from 3M Company, St. Paul, U.S.A.

The fastening means 15 may be attached to the backing 20 by adhesive bonds, sonic bonds, thermal bonds or any other attachment means.

The loop material may be comprised of woven or non-woven fabric or any other suitable material which interlocks with the contemplary hook fastener material. Suitable loop fastening materials of a knitted or extrusion-bonded type, respectively, are commercially available, for example, from 3M Company, St. Paul, U.S.A.

In case the fastening means 15 comprises the hook fastener means, it may be necessary and/or desirable to apply a patch of contemplary loop material as a landing zone 5 in the waistband portion of the absorbent article as is schematically shown, for example, in FIG. 1. In other cases such as, for example, where the outer surface 3$b$ of the back sheet 3 is formed by a non-woven material, the mechanical fastening means 15 may be selected to interact directly with the outer surface 3$b$ of the back sheet 3 so that a separate landing zone is not required. In case of adhesive fastening means 15 it may be necessary or desirable to include a separate landing zone 5 for receiving an adhesive attachment of the fastening means thereon.

Useful adhesives for use in adhesive layers 16, 16$a$ and/or as an adhesive fastening means 15, include pressure-sensitive adhesives including pressure-sensitive adhesive hot-melt adhesives and non-pressure-sensitive adhesives. Suitable pressure-sensitive adhesives include rubber-based adhesives (also called rubber-resin adhesives) which comprise natural or synthetic rubber materials and typically also tackifying resins in order to render the rubber materials tacky. Preferred examples of rubber-based pressure-sensitive adhesives are the polystyrene polyisoprene block copolymers tackified with synthetic polyterpene resins. Suitable pressure-sensitive adhesives furthermore include acrylate-based pressure-sensitive adhesives such as, for example, those disclosed in US Reissue 24,906 or U.S. Pat. No. 4,710,536. The thickness of the adhesive layers 16, 16$a$ preferably is between 10 and 200 µm and more preferably between 20 and 100 µm.

The shape of the fastener portion 10 can vary broadly. Fastener strips which are applied to side panels of the diaper, may have an essentially rectangular shape which can be varied by applying shaped cuttings. This is exemplified, for example, in FIG. 4 where ellipsoid cuttings are applied to a continuous web of twin fastener portion 10$a$. Shaped cuttings can also be applied to single fastener portions 10, and the shape of the cutting may vary and includes regular and irregular shapes.

The fastener portion 10 may comprise other components such as, for example, fingerlifts, cover means to partially cover an adhesive means or so-called release tapes which are provided to reliably secure the fastener portion 10 in a Y-type bonding to the diaper.

Figure 2:
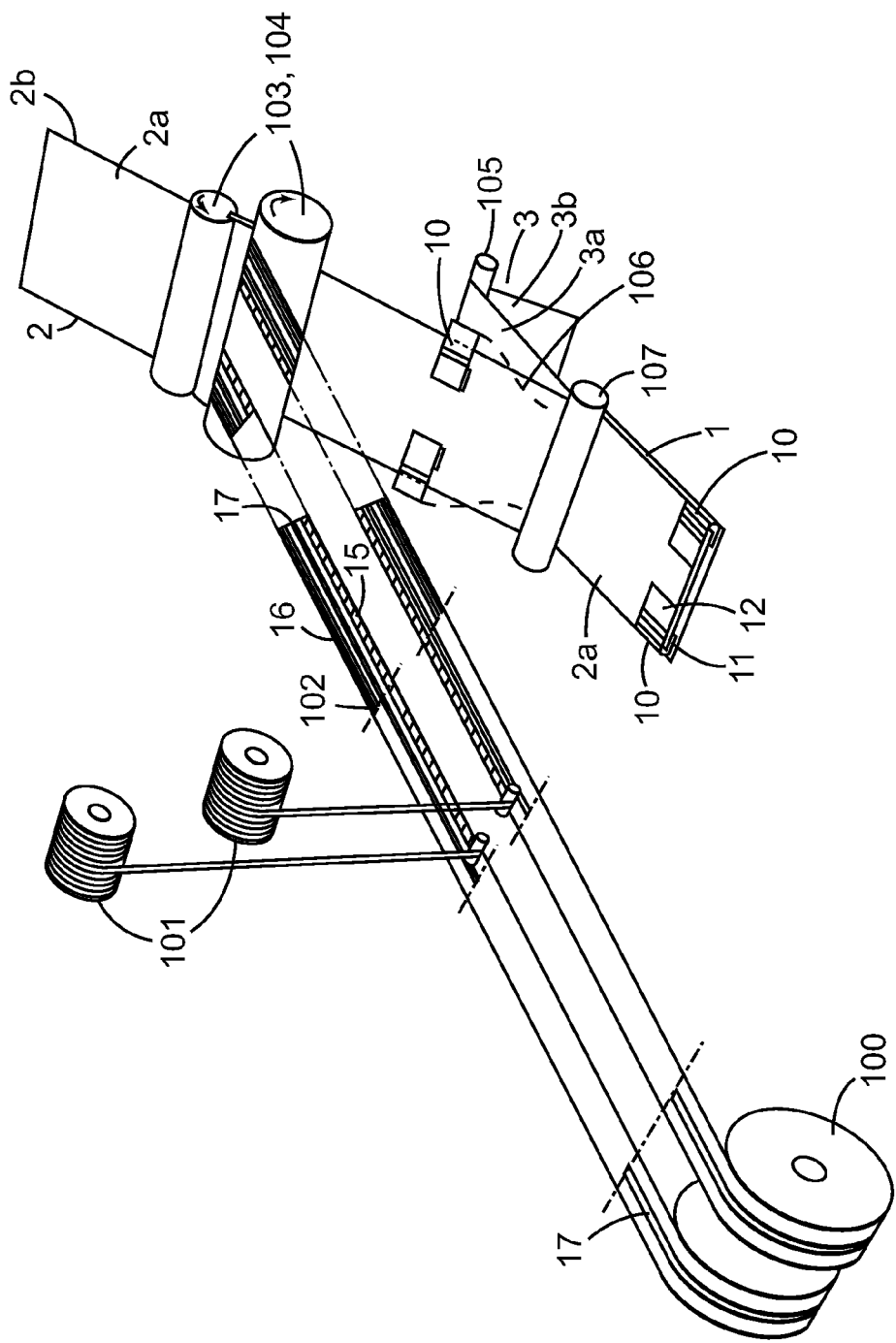
FIG. 2 is a schematic representation of an embodiment of the method of the present invention which is operated continuously and which comprises providing a continuous web of top sheet 2 having an inner surface 2*a* and an outer surface 2*b*, placing a pair of two fastener portions 10 in intervals in machine direction MD onto the inner surface 2*a* of the top sheet 2, folding around the manufacturer's end along the lateral edge 2*c* of the top sheet 2 and applying a continuous back sheet 3 through its inner surface 3*a* onto the outer surface 2*b* of the top sheet 2 to provide a continuous web of an absorbent article 1 which can be cut into separate absorbent articles 1.

FIG. 2 schematically discloses a particular method of manufacturing a specific example of a fastener portion 10. A schematic cross-sectional view of such fastener portion is shown in FIG. 3. In the specific embodiment of FIG. 2, a backing 20 comprising an elastic means 17 is unwound from support roll 100. A mechanical fastening means 15 is unwound from supply roll 101 and attached to the backing, for example, by an adhesive layer. An adhesive layer 16 is applied to the manufacturer's end 11 of the backing by the coating head of adhesive applicator 102 (details not shown in FIG. 2). Alternatively, it is also possible to use a backing which is pre-coated in strip form with an adhesive layer 16. It may also be possible to omit the adhesive layer 16 if the manufacturer's end 11, for example, is secured between the top sheet 2 and the back sheet 3 of the absorbent article and if such top sheet 2 and/or back sheet 3 comprise adhesive layer(s) for bonding them to each other.

The fastener portion 10 thus obtained is then applied to the top sheet web 2 by means of the cut and place applicator 103, 104 comprising a vacuum roll 103 and a rotating knife 104.

The above description of the absorbent article 1 is meant to be explanatory only and not limiting. The absorbent article 1 is described here only to an extent required to explain the present invention but it is understood that the absorbent article 1 usually comprises a variety of further components and features including, for example, but not restricted to a crotch region 8 often comprising leg elastic members arranged to draw and hold the diaper against the legs of the wearer, elastic means in the front and/or rear waistband area 7a, 7b and/or the fastener portion 10, to ensure a tight fit of the absorbent article around the wearer's waist, elasticized containment flaps arranged, for example, laterally inboard from the leg elastics along the machine direction to support containment of exudates and so on.

Likewise, the above description of the fastener portion 10 is meant to be explanatory only and not limiting.

Further details on diapers and their construction are described in literature and may be taken, for example, from U.S. Pat. No. 5,399,219, WO 96/10,382 or EP 0,529,681. Examples for the construction of fastener portion 10 are given, for example, in WO 99/03,437, EP 0,321,232 or U.S. Pat. No. 5,399,219.

While the design and construction of the fastener portion 10 used in the present invention may be conventional the present invention provides a novel method for applying a fastener portion 10 to an absorbent article 1.

In a first alternative A of the method according to the present invention the fastener portion 10 is positioned in a first step on the inner surface 2a of the top sheet 2 so that the user's end 12 is essentially supported by the top sheet 2 and the manufacturer's end 11 is essentially adjacent to one of the edges 2c, 2d of the top sheet whereby the fastener means 15 is facing towards the inner surface 2a of the top sheet 2. The term "adjacent" includes that the manufacturer's end 11 may essentially project over one of the edges 2c, 2d of the top sheet as is, for example, shown schematically in FIG. 2 for a specific construction of the absorbent article 1. In FIG. 2, the top sheet 2 is provided as a continuous web with its inner surface 2a facing upwards. The web passes cut and place applicator 103, 104 where a pair of two fastener portions 10 is placed adjacent to the opposite lateral edges 2c, 2d of the top sheet 2 so that the manufacturer's ends 11 of the fastener portions 10 project over the corresponding edges 2c, 2d; correspondingly the user's ends 12 of the fastener portions 10 are supported by the top sheet so that the outboard edges of the user's ends 12 in cross-direction essentially match with the corresponding edges 2c, 2d of the top sheet 2. The pair of fastener portions 10 is supplied discontinuously by means of cut and place applicator 103, 104 so that the fastener portions 10 are placed on areas of the continuous web of top sheet 2 forming the waistband portion or portions of the resulting absorbent article 1. If desired, the user's end of fastener portion 10 may be temporarily held in place on the top sheet web 2, for example, by mechanical means such as plates, bars or belts until its manufacturer's end 11 is secured to the absorbent article as described below.

In a second step of the method according to the present invention, the manufacturer's end 11 of the fastener portion is secured to the absorbent article. In the specific embodiment of the method schematically shown in FIG. 2, the manufacturer's end is folded by essentially 180° around the edge 2c, 2d of the top sheet 2 so that it is subjacent to the outer surface 2b of the top sheet and essentially opposite to the user's end 12. The manufacturer's end 11 is secured between top sheet 2 and back sheet 3 which is supplied as a continuous web with its inner surface 3a facing towards the outer surface 2b of the top sheet 2. The top sheet 2 and the back sheet 3 are laminated together between the pair of rollers 107 (only one roller shown) to give a continuous web of absorbent article 1.

An enlarged cross section through the circled area of the waistband portion of the absorbent article 1 is shown in FIG. 3. The absorbent article 1 comprises a top sheet 2 and a back sheet 3 sandwiching an absorbent core 4 (not shown in FIG. 2). The manufacturer's end 11 of the fastener portion 10 is arranged between the top sheet 2 and the back sheet 3. The manufacturer's end 11 of the fastener portion 10 is secured to the outer surface 2b of the top sheet 2 through adhesive layer 16 and the back sheet 3 is bonded to the manufacturer's end 11 of the fastener portion 10, to the top sheet 2 and to the absorbent core 4 by means of adhesive layer 16a The user's end 12 of the fastener portion 10 can be conceptionally divided into a grip portion 12' and an intermediate portion 12" located between the grip portion 12' and the manufacturer's end 11. The grip portion 12' includes in the specific embodiment of FIG. 2 and 3 elastic means 17, fastening means 15 and a fingerlift portion at the inboard end of the grip portion 12'.

The specific embodiment of alternative A of the method of the present invention schematically represented in FIG. 2 and 3 is to merely illustrate the invention without restricting it in any way. It is, for example, not required that the manufacturer's end 11 essentially projects over the edge 2c, 2d of the top sheet 2 but the manufacturer's end 11 can be partly or fully supported by the top sheet 2. In this case, when folding over the manufacturer's end 11, the underlying part of the top sheet 2 would be folded over, as well. It is, for example, also not required that the manufacturer's end when folded over, is arranged between the top sheet 2 and the back sheet 3 but it is also possible that the top sheet 2 and the back sheet 3 are laminated first, followed by folding over of the manufacturer's end and adhering it to the outer surface 3b of the top sheet. Securing of the manufacturer's end 11 of the fastener portion 10 to the absorbent article 1 and bonding of the top sheet 2 and the back sheet 3 can be affected through attachment means other than adhesive bonds. The fastener portions 10 may be secured to other portions of the diaper as well. It is also possible, for example, to apply one fastener portion 10 only to each of the front and rear waistband portions 7b, 7a or to apply a pair of fastener portions 10 to each of the front and rear waistband portions 7b, 7a.

While FIG. 2 and 3 are understood to be explanatory but not limiting, they illustrate the gist of the present invention which resides in providing a method for assembling a fastener portion 10 to an absorbent article 1 comprising:

placing the fastener portion 10 onto the top sheet 2 or the back sheet 3, respectively, of the absorbent article 1 so that the user's end 12 of the fastener portion 10 is supported by the top sheet 2 or the back sheet 3 and preferably is arranged already in the position it assumes when the absorbent article is being stored, before manipulating in a subsequent step the manufacturer's end 11 so that it can be secured to the diaper.

In the state of the art, the manufacturer's end has been assembled to the diaper first followed by manipulating the user's end to bring it into its final storage position.

The method of the present invention is specifically suited to be applied under high speed manufacturing conditions. Since the user's end is supported by the top sheet 2 or the back sheet 3, respectively, during the assembling of the fastener portion 20 to the absorbent article, the method of the present invention is especially advantageous for applying fastener portions 10 comprising elastic means.

In a second alternative B of the method according to the present invention, the fastener portion 10 is positioned in a first step on the outer surface 3b of the back sheet 3 so that the user's end 12 is essentially supported by the top sheet 2 and the manufacturer's end 11 is essentially adjacent to one of the edges 3c, 3d of the back sheet 3 whereby the fastener means 15 is facing outwards. Subsequently, in a second step, the manufacturer's end 11 of the fastener portion 10 is folded over as has been described above.

In an especially advantageous embodiment of the present invention, a twin fastener portion 10a is used comprising a first and a second manufacturer's end 11a, 11b which are connected by user's ends 12a, 12b and a releasable connection 19, wherein the dimensions of the manufacturer's ends 11a, 11b, the user's ends 12a, 12b and the releasable connection 19 in cross-direction being selected so that the manufacturer's ends 11a, 11b can be positioned adjacent to opposite edges 2c, 2d and/or 3c, 3d of the top sheet 2 or the back sheet 3, respectively. In the twin fastener portion 10a, the user's ends 12a and 12b are connected through a releasable connection 19 which can be removed to provide two separate fastener portions 10.

Twin fastener portions 10a wherein the releasable connection 19 is formed by an additional separate part, are disclosed in WO 84/04,242. In one of the two embodiments of WO 84/04,242, the releasable connection is a perforated adhesive strip which is adhered to the user's ends 12a, 12b directly or by a separate Z-folded fixing strip. The perforated adhesive strip can be broken to provide two separate fastener portions 10. In the second embodiment of WO 84/04,242, the releasable connection is a removable tape which is adhered to the user's ends 12a, 12b directly or by a separate Z-folded fixing strip. The removable tape is peeled off to provide two separate fastener portions 10.

While the twin fastener portions disclosed in WO 84/04, 242 can be used in the method of the present invention, it was found by the present inventors that twin fastener portions 10a wherein the two user's ends 12a, 12b are directly releasably connected to each other without an additional separate part which has to be removed and discarded, are especially preferred. These constructions are easy to handle under high speed manufacturing conditions and do not result in additional waste when breaking the releasable connection 19. Twin fastener portions wherein the two user's ends 12a, 12b are directly connected to each other through a releasable connection 19 with the proviso that such releasable connection 19 does not comprise a separate part, are new and they are subject matter of the present invention.

The releasable connection 19 preferably is a weak line such as, for example, a perforation arranged directly between the two user's ends 12a, 12b. The weak line connects the user's ends 12a and 12b in the twin fastener portions 10a but can easily be removed such as, for example, broken to release a pair of separate fastener portions 10 without creating any additional waste. In another embodiment, the two user's ends 12a,12b may also, for example, overlap over a small distance whereby the two user's ends 12a,12b are releasably connected to each other in such overlapping area, for example, by means of ultrasonic bonding spots or a little spot of wax or removable adhesive which do not need to be removed and discarded upon breaking of such temporary bond but can be left in place.

Figure 4:
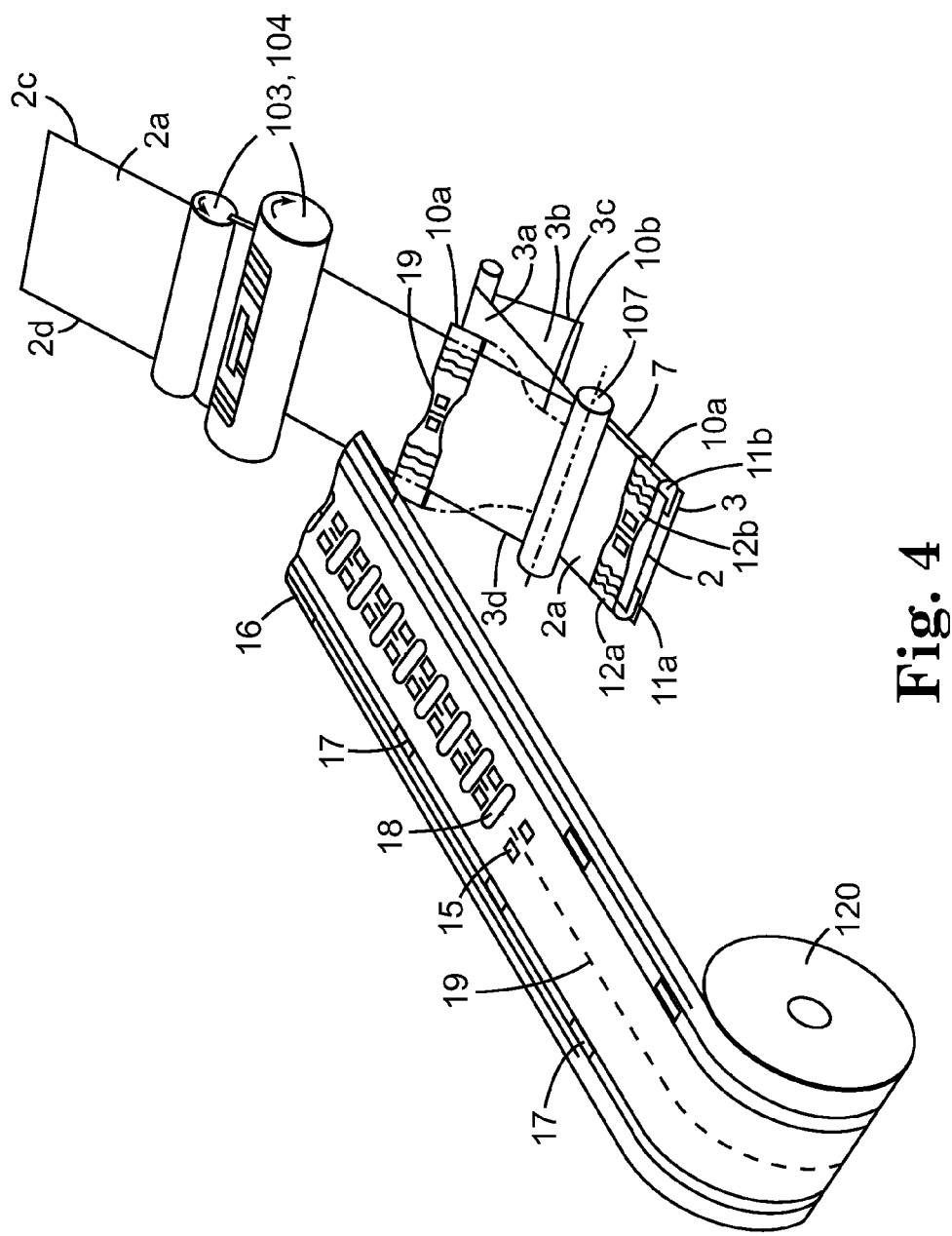
FIG. 4 is a schematic representation of another embodiment of the method of the present invention which is operated continuously and differs from the method of FIG. 2 in that one twin fastener portion 10*a* is used instead of the pair of two separate fastener portions 10, said twin fastener portion 10*a* comprising a releasable connection 19.

A specific embodiment of the novel twin fastener portions 10a according to the present invention where the releasable connection 19 does not comprise a separate part, is schematically shown in form of a continuous web in the left part of FIG. 4. In this schematic embodiment, the twin fastener portion 10a is coated with an adhesive layer 16 on each of the manufacturer's ends 11a, 11b and comprises an elastic means 17 and a fastening means 15 on each of the user's ends 12a, 12b. The releasable connection 19 is formed by perforated line 19. The shape of two neighbouring twin fastener portions is modified by applying shaped cuttings 18.

The graphic representation of FIG. 4 is intended to illustrate the present invention without limiting it. The releasable connection 19, for example, can also be formed by a wavy perforated line resulting in separate fastener portions 10 having curved fingerlifts.

The various components of the twin fastener portion 10a such as the fastening means 15, the elastic means 17, the backing, the adhesive layer 16 and so on may be formed, for example, by the materials disclosed for single fastener portions 10 above but other materials may be used, as well.

The preferred method of the present invention employing twin fastener portions 10a is illustrated by the non-limiting schematic representation of FIG. 4 where twin fastener portions 10a are unwound from the roll 120 and applied to the inner surface 2a of the top sheet 2 which is provided as a continuous web. The twin fastener portions 10a are applied to the inner surface 2a of the top sheet via a place and cut applicator 103, 104 in a discontinuous way so that the twin fastener portions 10a are placed on areas of the continuous web of top sheet 2 forming one of the waistband portions 7a, 7b or both waistband portions 7a, 7b of the resulting absorbing article 1, respectively. The twin fastener portions 10a are placed on the top sheet 2 so that their user's ends 12a, 12b are supported by the top sheet 2 and the two opposed manufacturer's ends 11a, 11b are adjacent to the opposed edges 2c, 2d of the top sheet. The subsequent step of folding over the manufacturer's ends is schematically shown for two different constructions in FIG. 5a and 5b.

In FIG. 5a, the manufacturer's ends 11a, 11b of the twin fastener portion 10a are essentially fully supported by the top sheet 2 so that the outboard ends of the manufacturer's ends 11a, 11b essentially match with the edges 2c, 2d of the top sheet 2 while the lateral extension of the back sheet 3 is smaller than that of the top sheet 2 by about the sum of the extensions of the manufacturer's ends 11a, 11b in total. The manufacturer's ends 11a, 11b are then folded over together with the underlying portions of the top sheet 2 so that the configuration shown in FIG. 5a' is obtained.

In FIG. 5b the manufacturer's ends 11a, 11b essentially project over the edges 2c, 2d of the top sheet 2 so that only the manufacturer's ends 11a, 11b are folded over. In the configuration shown in FIG. 5b', the manufacturer's end 11 is positioned between the top sheet 2 and the back sheet 3. It would also be possible, however, that the top sheet 2 and the back sheet 3 are laminated first, and that the manufacturer's end 11 is then folded over to adhere to the outer surface 3b of the top sheet.

The use of twin fastener portion 10a is advantageous because, for example, in the method of manufacturing of FIG. 4 only one fastener portion 10a needs to be applied as opposed to two fastener portions in the corresponding method of FIG. 2. Also the releasable connection is usually removed only by the end user so that the user's ends are reliably prevented from "popping open" during the manufacturing and storage of the diaper.

It is, however, also possible that the twin fastener portion 10a is broken into two separate fastener portions 10 during the manufacturing of the diaper as is shown schematically for a specific construction in FIG. 6. In FIG. 6, the twin fastener portion 10a has been applied to a top sheet 2 comprising a fold 2e. In this specific embodiment, the manufacturer's ends 11a, 11b have been folded around prior to the application of the twin fastener 10a so that the manufacturer's ends are adhered to the inner surface 2a of the top sheet 2. It is, however, also possible that the manufacturer's ends are folded around so that they are located opposite to the user's ends 12a, 12b and subjacent to the outer surface 2b of the top sheet.

In the upper part of FIG. 6, the releasable connection 19 of the twin fastener portion 10a has not been broken yet; the twin fastener portion 10a has been applied to the top sheet and the manufacturer's ends 11a have been folded over. In the next step which is shown in the lower part of FIG. 6, the releasable connection 19 is broken by exerting lateral forces in cross-direction onto the top sheet 2 to straighten out fold 2e. Subsequently to this, the back sheet 3 is laminated to the top sheet as is schematically indicated in FIG. 6.

We claim:

1. Method of applying one or more twin fastener portions 10a to an absorbent article 1 and, in particular, to a disposable diaper, said absorbent article 1 comprising a top sheet web 2 having an inner surface 2a, an outer surface 2b, a first lateral edge 2c and a second lateral edge 2d, a back sheet 3 having an inner surface 3a, an outer surface 3b, a first lateral edge 3c and a second lateral edge 3d, an absorbent core 4 arranged between said top sheet 2 and said back sheet 3, said twin fastener portion 10a comprising a first manufacturer's end 11a, a first user's end 12a, a releasable connection 19, a second user's end 12b and a second manufacturer's end 11b, wherein the dimensions of the manufacturer's ends 11a, 11b, the user's ends 12a, 12b and the releasable connection 19 in cross-direction being selected so that the manufacturer's ends 11a, 11b can be positioned adjacent to opposite lateral edges 2c, 2d and/or 3c, 3d of the top sheet 2 or the back sheet 3, respectively, and wherein the releasable connection 19 can be released to provide two separate fastener portions 10, said method comprising in a first alternative (A) the steps of:

(i) providing a top sheet 2,
(ii) placing the one or more twin fastener portions 10a onto the inner surface 2a of the top sheet 2 so that the user's ends 12a, 12b and the releasable connection 19 are essentially supported by the top sheet 2 and the manufacturer's ends 11a, 11b are essentially adjacent to opposite edges 2c, 2d of the top sheet 2 whereby the fastening means 15a, 15b are facing towards the inner surface 2a of the top sheet 2,
(iii) folding around the manufacturer's ends 11a, 11b, and
(iv) applying an absorbent core 4 and a back sheet 3 onto the top sheet 2, whereby the sequence of steps (ii) and (iii) or (iii) and (iv), respectively, may be exchanged, or in a second alternative (B)

(i) providing a back sheet 3,
(ii) placing the one or more twin fastener portions 10a onto the outer surface 3a of the back sheet 3 so that the user's ends 12a, 12b and the releasable connection 19 are essentially supported by the back sheet 3 and the manufacturer's ends 11a, 11b are essentially adjacent to opposite lateral edges 3c, 3d of the back sheet 3 whereby the fastening means 15 are facing outwards,
(iii) folding around the manufacturer's ends 11a, 11b, and
(iv) applying an absorbent core 4 and a top sheet 2 onto the back sheet 3, whereby the sequence of steps (ii) and (iii) or (iii) and (iv), respectively, may be exchanged and wherein the top sheet 2 in the first alternative (A), step (ii) comprises a fold 2e or wherein the back sheet 3 in the second alternative (B), step (ii) comprises a fold, respectively, whereby such folds are straightened out in subsequent steps during or after the application, respectively, of the twin fastener portion 10a, by exerting a force in cross direction on at least the top sheet 2 or the back sheet 3, respectively, thereby breaking the twin fastener portion 10a into two separate fastener portions 10.

2. Method according to claim 1 wherein the one or more twin fastener portions 10a are applied to the rear waistband portion 7a and/or to the front waistband portion 7b.

3. Method according to claim 1 wherein the one or more twin fastener portions 10a are applied intermittently to a continuously running web of a top sheet 2 or back sheet 3, respectively, to provide a continuously running web of an absorbent article 1 from which separate absorbent articles 1 can be cut.

* * * * *

UNITED STATES PATENT AND TRADEMARK OFFICE
CERTIFICATE OF CORRECTION

PATENT NO. : 7,214,285 B2
APPLICATION NO. : 10/491775
DATED : May 8, 2007
INVENTOR(S) : Werner T. Guenther It is certified that error appears in the above-identified patent and that said Letters Patent is hereby corrected as shown below:

Title page,
Item [57], ABSTRACT, Line 7, Delete "manufacture's" and insert -- manufacturer's --, therefor.
Item [57], ABSTRACT, Line 8, Delete "2c,2d" and insert -- 2c, 2d --, therefor.

Column 1,
Line 31, Before "waistband" delete "front." and insert -- front --, therefor.

Column 2,
Line 57, Delete "2c,2d" and insert -- 2c, 2d --, therefor.

Column 4,
Line 46, Delete "103,104" and insert -- 103, 104 --, therefor.
Line 47, Delete "knive" and insert -- knife --, therefor.

Column 5,
Line 3, Delete "respectively, to" and insert -- respectively --, therefor.

Column 6,
Line 33, Delete "Alterative" and insert -- Alternative --, therefor.

Column 9,
Line 43, Delete "engagable" and insert -- engageable --, therefor.

Column 12,
Line 11, After "16a" insert -- . --.

Column 13,
Line 53, Delete "12$a$,12$b$" and insert -- 12a, 12b --, therefor.
Line 55, Delete "12$a$,12$b$" and insert -- 12a, 12b --, therefor.

UNITED STATES PATENT AND TRADEMARK OFFICE
CERTIFICATE OF CORRECTION

PATENT NO. : 7,214,285 B2
APPLICATION NO. : 10/491775
DATED : May 8, 2007
INVENTOR(S) : Werner T. Guenther It is certified that error appears in the above-identified patent and that said Letters Patent is hereby corrected as shown below:

Column 16,
Line 32, In Claim 2, before "rear" delete "the" and insert -- a --, therefor.
Line 33, In Claim 2, before "front" delete "the" and insert -- a --, therefor.

Signed and Sealed this

Fourteenth Day of August, 2007

JON W. DUDAS
*Director of the United States Patent and Trademark Office*